United States Patent
Martens et al.

(10) Patent No.: US 10,466,223 B2
(45) Date of Patent: Nov. 5, 2019

(54) METHOD FOR TESTING A PUMPING DEVICE IN A GAS-MEASURING SYSTEM

(71) Applicant: Dräger Safety AG & Co. KGaA, Lübeck (DE)

(72) Inventors: Matthias Martens, Groß Schenkenberg (DE); Hans-Ullrich Hansmann, Barnitz (DE); Karsten Hiltawsky, Stockelsdorf (DE); Kai Einecke, Berkenthin (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 104 days.

(21) Appl. No.: 15/358,817

(22) Filed: Nov. 22, 2016

(65) Prior Publication Data

US 2017/0146505 A1    May 25, 2017

(30) Foreign Application Priority Data

Nov. 25, 2015 (DE) .......................... 10 2015 015 153

(51) Int. Cl.
| | |
|---|---|
| *G01N 33/00* | (2006.01) |
| *F04D 25/00* | (2006.01) |
| *F04B 51/00* | (2006.01) |
| *F04D 25/06* | (2006.01) |
| *F04D 27/00* | (2006.01) |

(52) U.S. Cl.
CPC ......... *G01N 33/0073* (2013.01); *F04B 51/00* (2013.01); *F04D 25/00* (2013.01); *F04D 25/06* (2013.01); *F04D 27/001* (2013.01)

(58) Field of Classification Search
CPC .. F04B 49/02; F04B 2203/00; F04B 2203/02; F04B 51/00; G01N 33/0073; F04D 25/00; F04D 25/06; F04D 27/001
See application file for complete search history.

(56) References Cited

U.S. PATENT DOCUMENTS

| | | | |
|---|---|---|---|
| 6,167,965 B1* | 1/2001 | Bearden | E21B 43/121 166/105.5 |
| 2007/0196213 A1* | 8/2007 | Parsons | F04B 49/065 417/32 |
| 2010/0034665 A1* | 2/2010 | Zhong | F04D 15/0066 417/42 |
| 2011/0221820 A1* | 9/2011 | Shibata | B41J 2/04563 347/17 |

FOREIGN PATENT DOCUMENTS

| | | |
|---|---|---|
| DE | 198 45 441 A1 | 4/2000 |
| DE | 699 02 327 T2 | 11/2002 |
| DE | 10 2006 048 430 A1 | 5/2007 |
| DE | 10 2005 045 272 B4 | 10/2007 |

* cited by examiner

*Primary Examiner* — Matthew G Marini
(74) *Attorney, Agent, or Firm* — McGlew and Tuttle, P.C.

(57) ABSTRACT

A method and system for testing a pumping device (9) with a control unit (91) in a gas-measuring system (1). The pumping device (9) is tested with the control unit (91), which is configured to test readiness of the pumping device (9) to operate. An initialization data set and an operating data set are used for the testing. An indicator of readiness of the pumping device (9) to operate is determined based on this.

18 Claims, 2 Drawing Sheets

METHOD FOR TESTING A PUMPING DEVICE IN A GAS-MEASURING SYSTEM

CROSS REFERENCE TO RELATED APPLICATIONS

This application claims the benefit of priority under 35 U.S.C. § 119 of German Application 10 2015 015 153.3 filed Nov. 25, 2015, the entire contents of which are incorporated herein by reference.

FIELD OF THE INVENTION

The present invention pertains to a gas-measuring system with a gas-measuring device and with a pumping device.

BACKGROUND OF THE INVENTION

Gas-measuring systems and gas-measuring devices are used for industrial gas measurement and to protect persons who are present in areas or rooms from hazards to health and life. In an industrial environment, such as the petrochemical industry, refineries, chemical industry, industrial gas measurement is significant for monitoring explosive or toxic gases or vapors. Both mobile and stationary devices are used. Combinations of mobile or stationary devices are also used to make it possible to perform measurements, gas concentrations or gas analyses in storage tanks, boreholes or silos. Thus, a combination of a mobile gas-measuring device with a charging station for supplying electrical energy as well as with a pump is known from DE 10 2005 045 272 B4. It is thus possible to also use mobile gas-measuring devices for measuring gas concentrations in a drawing shaft or in a borehole by the gas concentration being able to be fed by means of the pump via a long flexible tube from the borehole to the surface to the mobile gas-measuring device. The control of the pump with the start of feeding, the flow rate and further operating properties of the pump is performed by the mobile gas-measuring device or the control thereof. It is essential and necessary for carrying out gas measurements by means of pumps during the operation to have information available on the readiness of the pump to operate. For example, contaminated fine dust or particle filters, as well as porous hose pipes or wear on the mechanical bearings of the pump may affect the readiness of the pump to operate.

SUMMARY OF THE INVENTION

In the knowledge of the above-mentioned known state of the art and analysis of the drawbacks of the known state of the art, an object of the present invention is therefore to provide a method for testing a pumping device in a gas-measuring system.

Another object of the present invention is to provide a method that makes it possible to detect changes in the operating properties of the pumping device.

These and other objects are accomplished with a method for testing a pumping device in a gas-measuring system according to the invention. The method for testing a pumping device comprises providing the pumping device comprising a pump and a control unit arranged in the pumping device or associated with the pumping device and at least one data storage element. At least one first value characterizing a first operating state of the pumping device is determined by the control unit and the at least one first value is stored in the at least one data storage element as an initialization data set. At least one additional value characterizing an additional operating state is determined by the control unit and the at least one additional value is stored in at least one data storage element as an operating data set. The additional operating state follows the first operating state in time. The control unit compares the initialization data set and the operating data set with values characterizing the operating states of the pumping device. The control unit determines an indicator of readiness of the pumping device to operate on the basis of the comparison.

The present invention is based on the fact that a pumping device arranged in a gas-measuring system is operated, checked, controlled or regulated such as to detect the ability of the pumping device to function. To carry out the method according to the present invention for testing the pumping device, the pumping device has a control unit. This control unit is configured to carry out the method according to the present invention for testing the pumping device in the gas-measuring system. In addition to the control unit in the pumping device, with a pump, the pump, the corresponding switching devices or corresponding sensor system are involved as additional components for operating the pumping device. The switching devices/switching means and/or sensor system are, for example, one or more sensors or probes for measuring the speed of rotation, for measuring the electric current and/or voltage, for measuring the ambient pressure, for measuring the feed pressure, for measuring the flow or for temperature measurement. The pumping device additionally has at least one pump configured to feed a quantity of a fluid, gas or gas mixture, preferably with an electric pump motor or with a comparable drive for feeding the fluid, gas or gas mixture. The pumping device preferably has, in addition and in a typical configuration, a gas inlet intended and configured for drawing in gas through the pump as well as a gas outlet configured for releasing the fed quantity of a gas to the gas-measuring device.

The gas-measuring system, in which the pumping device is used, has, in addition to the pumping device according to the present invention, which is essential for the present invention, an analysis system, a gas-measuring device with a gas sensor system that is present in the gas-measuring device and is suitable for gas measurement, as well as components for the operation of the gas-measuring device.

Some of the terms used within the framework of this patent application will be explained in more detail as follows.

A data link is, in the sense of the present invention, a connection of at least two participants of a wired, wireless, optical connection, which is suitable for transmitting control signals, data signals or output signals. This also covers both direct physical connections (cabled connections, radio connections, optical light guide connections) as well as indirect or logical connections for transmitting information, control signals, data signals or output signals with physical or data technical conversions or transformations, voltages and currents. A control signal is defined in the sense of the present invention as an individual control signal, a control signal as part of a set of control signals, as well as as a plurality or a set of control signals. A data signal is defined in the sense of the present invention as an individual data signal, a data signal as part of a set of data signals, as well as a plurality or a set of data signals. An output signal is defined in the sense of the present invention as an individual output signal, an output signal as part of a set of output signals, as well as as a plurality or a set of output signals. An error signal is defined in the sense of the present invention as a signal or a set of signals which signal or which set represents a state concerning an error situation, a disturbance in the operation or an error in signal processing, signal detection or signal output or signal supply.

A gas to be measured is defined in the sense of the present invention as a gas or a gas mixture, which is such that the at least one gas sensor of the gas-measuring device is sensitive to a change in a gas concentration of this gas to be measured and responds to changes in the gas concentration of this gas to be measured with changes in the gas concentration measured value.

an indicator of the readiness of the pumping device to operate is determined by the control unit on the basis of the comparison.

The following tabular list in Table 1 shows which measured variables or manipulated variables of the sensors or probes cooperating in the pumping device during the operation, for example, in configurations of different embodiments, are suitable in themselves or in different combinations with one another as values to characterize the operating state of the pumping device and are relevant, advantageous and suitable for storage in operating data sets.

TABLE 1

A feed pressure generated by the pumping device, for example, in the form of a pressure difference in relation to a measuring environment (e.g., chemical plant, shop, building, industrial area) or in relation to a measuring location with an elevation different from that of the pump (e.g., tunnel, in-ground tank, storage tank, silo),
an ambient air pressure in the measuring environment or at the measuring location,
a composition of a gas mixture present in the measuring environment or at the measuring location,
an ambient humidity in the measuring environment or at the measuring location,
an ambient temperature in the measuring environment or at the measuring location,
an operating temperature of the pump,
a flow rate or mass flow rate fed by the pump,
a change over time in the flow rate or mass flow rate fed by the pump,
a flow velocity generated by the pump,
a speed of rotation n of the pump,
an electric operating current I of the pump motor,
an electric operating voltage U of the pump motor.

A resetting gas is defined in the sense of the present invention as a gas or a gas mixture that is such that the at least one gas sensor of the gas-measuring device is not sensitive to a change in the gas concentration of this gas or gas mixture and does not respond to changes in the gas concentration of this resetting gas with changes in the gas concentration measured value.

To carry out the method according to the present invention for testing a pumping device in a gas-measuring system, the control unit is provided as part of the pumping device or as a unit associated with the pumping device. Such a control unit is usually configured as a programmable or memory-programmable unit configured for programming, for example, in the form of a microprocessor ($\mu P$) microcomputer, microcontroller ($\mu C$) or in a comparable form of a memory-programmable controller (MPC) or of a programmable logic unit (ASIC, FPGA, PAL, GAL) and is, in addition, usually connected to at least one data storage element, such as volatile or non-volatile memory units (RAM, ROM, EEPROM) or removable media for data storage (SD card, CF card, USB stick) or is equipped with such elements.

To test the pumping device, the sensor system provides measured values, with which the control unit is capable of determining operating states of the pumping device.

In the method according to the present invention for testing a pumping device, in a sequence of steps,
  the control unit detects a value characterizing at least one, the first operating state of the pumping device in a first operating state and stores it in the at least one data storage element as an initialization data set,
  in another operating state, following the first operating state in time, the control unit detects at least one additional value characterizing the further operating state of the pumping device and stores it in the at least one data storage element as an operating data set,
  a comparison of the two data sets with the values characterizing the operating states of the pumping device is performed by the control unit, and The determined measured values or setting values for the speed of rotation, the feed pressure, the fed flow rate, the electric power consumption of the pump motor, the operating temperature of the pump as well as measured values for the environment, such as air pressure, ambient temperature or ambient humidity, are stored, quasi as a reference for the characteristic values of the first operating state for the initialization in the data sets in the first operating state of the pumping device during the initialization, for example, in a tabular form or as a characteristic.

During the operation of the pumping device, the measured values are determined again and repeatedly in the second operating state following the first operating state in time, for example, in a tabular form or as a characteristic, as respective additional values for the speed of rotation, feed pressure, fed flow rate, electric power consumption of the pump motor, air pressure, ambient temperature, ambient humidity, and stored in the operating data set. By a comparison of the data from the initialization data set and the operating data set, the control unit determines the current state of the pumping device and the indicator of readiness of the pumping device to operate.

Table 2 below shows the properties of the pumping device that can be analyzed by the control unit on the basis of characteristic values and/or measured variables.

In addition, Table 2 shows what conclusions and consequences arise for a state analysis of the pumping device as well as of the gas-measuring system with pumping device and gas-measuring device on the basis of the values, measured variables or manipulated variables listed in Table 1 as well as of combinations of a plurality of measured variables or manipulated variables and what messages can be outputted in the form of notes, warnings or alarms for a user on the basis of the state analysis.

TABLE 2

| Measured variable | Change in measured/ manipulated variable(s) | Analyzed property, measured variable | Operating state | Category | Message |
|---|---|---|---|---|---|
| Change in feed rate over time [dV/dt] & Pump feed pressure [Δp] | dV/dt: Slow reduction & Pump feed pressure ≥ desired range | Rise in pneumatic load. Possible causes Filter resistance high Particles in measuring lines Particles in pump | Pump at performance limit Load increase cannot be compensated | A | Warning: Replace filter |
| Change in flow rate over time [dV/dt] & Pump feed pressure [Δp] | dV/dt: Abrupt reduction & Pump feed pressure ≥ desired range | Abrupt increase in pneumatic load Blockage in measuring line or pump | Problem in measuring line, e.g., clogging | B | Note: Check measuring line |
| Change in flow rate over time [dV/dt] & Pump feed pressure [Δp] | dV/dt: Great increase & Pump feed pressure ≤ desired range | Leak in suction system Parallel to suction location | Gas to be measured is diluted | B | Warning: Measurement incorrect |
| Characteristic Speed of rotation n, Current I & Pump feed pressure [Δp] | Characteristics: Variation in flow rate dV/dt ± ΔdV/dt, Deviation from desired range | Wear or friction in motor | Wear in motor | C | Note: Replacement |
| Characteristic Speed of rotation n, Current I & Pump feed pressure [Δp] | Characteristics: Variation in speed of rotation Deviation from desired range | Wear or friction in motor | Wear in motor | C | Note: Replacement |

Further preferred embodiments of the method for testing the pumping device arise from the analyses listed in Table 2.

In a preferred embodiment, the control unit is configured to assign readiness of the pumping device to operate to categories in a further step. The categories are used to divide the operating states of the pumping device or to divide readiness of the pumping device to operate into critical situations, in which, for example, cleaning or maintenance with subsequent initialization is necessary; more critical situations, in which parts of the pumping device must be replaced shortly; and noncritical situations, which can be corrected, for example, within the framework of the next maintenance.

The categories are classified, as an example, to three stages in Table 2 above:
Non-critical situation A
Critical situation B
Very critical situation C.

In a preferred embodiment, an error signal is determined in an additional step by means of the control unit on the basis of the categories or on the basis of readiness to operate and the error signal is provided as an output signal by means of a data output unit.

In a preferred embodiment, an at least one first value characterizing the first operating state of the pumping device and/or the at least one additional value characterizing the at least one additional operating state of the pumping device is represented by at least one measured value or a setting value from a group of measured values or setting values. The group of measured values or setting values comprises:
a feed pressure generated by the pumping device,
an ambient air pressure,
an ambient humidity,
an ambient temperature,
a flow rate or mass flow rate fed by the pumping device,
a change in the flow rate or mass flow rate fed by the pumping device over time,
a velocity of flow generated by the pumping device,
a vacuum generated by the pump,
a speed of rotation of the pumping device or of a pump motor arranged in the pumping device or associated with the pumping device,
an electrical operating current of the pump motor, and
an electrical operating voltage of a pump motor arranged in the pumping device or associated with the pumping device.

In another preferred embodiment, the at least one first value characterizing a first operating state of the pumping device and/or the at least one additional value characterizing the at least one additional operating state of the pumping device is represented by at least one measured value or by a setting value from a group of the measured values or setting value, by a combination or by a pair of values of at least two measured values or setting values from the group of the measured values or setting values.

In a preferred embodiment, values characterizing additional working points deviating from a first working point are determined by the control unit in the first operating state and stored in the initialization data set.

In a special variant of this preferred embodiment of the method, values characteristic of different speeds of rotation are determined by means of the control unit at different working points in the first operating state and are stored in the initialization data set. The generation of a data set characterizing the first operating state and the storage thereof in the initialization data set are thus made possible.

Values for the speed of rotation, feed pressure, fed flow rate, electrical power consumption of the pump motor, air pressure, ambient temperature, ambient humidity are determined in this way for additional working points with a deviating speed of rotation, especially for a working point with a reduced speed of rotation and/or for a working point with an increased speed of rotation and stored in the initialization data set. A desired range with a corresponding tolerance zone is thus obtained for the values in the initialization data set. For example, a deviation is obtained in practice in the range of 3% to 10% for the reduced speed of rotation and the increased speed of rotation.

In another preferred embodiment, the control unit is configured to carry out in the first and/or second operating state a conversion of at least one of the measured values or setting values from the group of the measured values or setting values into measured values or setting values based on standardized environmental conditions. For example, measured temperature values, measured pressure values, measured humidity values, measured flow values are related now to so-called standardized conditions, such as STPD conditions (STPD=standard temperature, pressure, dry), to an ambient pressure of 1,013 hPa, 0° C. and a water vapor partial pressure $p(H_2)$ of 0 kPa (dry). An alternative standardization is, for example, a standardization to STP conditions (STP=standard temperature, pressure) according to DIN 1343, in which case the moisture content is not taken into account. Other alternative conversions arise from a selection of temperatures suitable for the operation of the gas-measuring system, of temperatures suitable for the pumping device, for example, 20° C. or 25° C. and/or pressure values, for example, 1,113 hPa, in order to also include, for example, a feed pressure at a preferred working point (speed of rotation, motor current) of the pump in the standardization.

In another preferred embodiment, the at least one first value characterizing a first operating state of the pumping device and/or the at least one additional value characterizing the at least one additional operating state of the pumping device is represented by at least one measured value or a setting value from a group of the following measured values or setting values, by a family of characteristics or a characteristic diagram, based on at least two measured values or setting values from the group of the measured values or setting values.

In a preferred embodiment of the method, the change in the feed rate over time, dV/dt, is measured as a volume flow and the corresponding pressure generated by the pumping device (vacuum or feed pressure) Δp is measured. The pressure generated by the pump now represents the physical cause of the feed of gas or gas mixture of a mass flow or volume flow as a difference in pressure relative to the pressure in the measuring environment or at the measuring location. The change in the flow rate over time, dV/dt, and the pressure characterize in this case the first operating state and are determined by the control unit in the first operating state. The control unit determines from this a ratio Δp to dV/dt as an initial pneumatic resistance value $Rp_i=\Delta p/[dV/dt]$ and stores this in the at least one data storage element in the initialization data set. An additional pneumatic resistance value $Rp_x$ is determined by the control unit in the second operating state and is stored in the at least one data storage element in the operating data set. A comparison of the two data sets with the pneumatic resistance values $Rp_i$, $Rp_x$ characterizing the operating states of the pumping device is subsequently performed by the control unit and an indicator of readiness of the pumping device to operate is determined on the basis of the comparison.

If great differences are obtained for the pneumatic resistance value between the initialization data set $Rp_i$ and the operating data set $Rp_x$, at least one of the components in the gas-measuring system has changed. If the pneumatic resistance value drops in the second operating state, i.e., during the operation, it can be inferred from that that the cause of this drop in the pneumatic resistance value is based on a leak in the gas-measuring system. This leak may lead to a great dilution of the gas to be measured and thus make it difficult to reliably detect higher gas concentrations and/or to qualitatively detect low gas concentrations. An indicator of readiness of the pumping device to operate can thus be determined, and this indicator can then optionally be outputted as a message in the form of a warning, as is shown, for example, in Table 2, against an incorrect measurement with dilution of the gas to be measured, or of a warning that there is a leak in or at the pumping device or the measuring line.

If the pneumatic resistance value increases during the operation, it can be inferred from this that the cause of this rise in the pneumatic resistance value Rp is based on an increase in a filter resistance or on a nearly complete clogging in the measuring line. A slow rise in the pneumatic resistance can be assumed to be due to a filter becoming gradually clogged, and an optional message may be sent in the form a note that it will soon become necessary to replace the filter (see Table 2).

A nearly complete clogging in the measuring line or a defect in or at the pumping device itself may occur if the increase in the pneumatic resistance value takes place suddenly or abruptly. Such a defect in or at the pumping device can be tested by a maneuver during the operation and can be distinguished from a clogging in the measuring line, in principle, by the fact that the pneumatic resistance value remains largely constant in case of a clogging in the measuring line in case of a change in the working point of the pump, while a defective pump can be detected from different pneumatic resistance values at different working points. Based on this distinction, a message (see Table 2) may optionally be outputted in the form of a note for checking the measuring line or of a note that it will soon become necessary to replace the pumping device.

In another, especially preferred embodiment, a plurality of measured variables or variables derived from the measured variables are analyzed with one another by the control unit, preferably in the form of a characteristic or of a functional relationship, combined with one another, and readiness of the pumping device to operate is determined based on this and an indicator of readiness of the pumping device to operate is determined. The values characterizing the first operating state and/or the at least one second operating state are obtained in this additional preferred embodiment from a combination from at least two measured variables, manipulated variables or from variables derived from the at least two measured variables. Such combinations may be defined or configured as pairs of values, functional relationships, characteristics, families of characteristics or characteristic diagrams.

For example, the following combinations are mentioned as examples for forming operating states in Table 3 below, which can be used as variables characterizing the pumping device:

TABLE 3

Volume flow [dV/dt] fed by the pump
combined with
the power consumption I of the pump motor
Operating temperature of the pump
combined with
the power consumption of the pump motor TABLE 3-continued Volume flow [dV/dt] fed by the pump
combined with
the speed of rotation n of the pump
Variation [ΔdV/dt] of the volume flow [dV/dt] fed
combined with
the speed of rotation n of the pump
Variation [ΔdV/dt] of the volume flow [dV/dt] fed
combined with
the power consumption I of the pump motor
Variation [ΔdV/dt] of the volume flow [dV/dt] fed
combined with
the power consumption I of the pump motor and combined with
the speed of rotation n of the pump
Variation [Δn] of the speed of rotation n of the pump
combined with
the volume flow [dV/dt] fed by the pump
Variation [Δn] of the speed of rotation n of the pump
combined with
the power consumption I of the pump motor
Variation [Δn] of the speed of rotation n of the pump
combined with
the volume flow [dV/dt] fed by the pump
and combined with
the power consumption I of the pump motor The determined indicator of readiness to operate may optionally be outputted as a message in the form of a note, warning or in another manner (see Table 2). In another preferred embodiment, the speed of rotation n of the pump, the pump current I or the pneumatic resistance Rp=[Δp/dV/dt] are determined as variables as respective functions of the volume flow dV/dt. So-called maneuvers are performed for this by the control unit. In the first or second operating state, n, I, Rp are measured for this by the control unit at a set dV/dt (volume flow working point 2). The variables n, I, Rp are subsequently measured and analyzed in a first variant of this additional preferred embodiment by means of the maneuver at a volume flow reduced by a volume flow difference [ΔdV/dt] (volume flow working point 1) and at a volume flow increased by a volume flow difference ΔdV/dt (volume flow working point 3). Essentially linear changes are typically obtained for the variables n and I when considering the three volume flow working points ([dV/dt−ΔdV/dt], dV/dt, [dV/dt+ΔdV/dt]). The value for the pneumatic resistance remains nearly constant at all three volume flow working points in an error-free case. The control unit carries out this maneuver with the three volume flow working points in the first operating state as well as in the second operating state, i.e., during the operation of the pumping device, and analyzes the results. If the pneumatic resistance as a function of the volume flow dV/dt does not remain constant or the speed of rotation n of the pump or the pump current I do not show a linear behavior as a function of the volume flow, a defect in the pump system, for example, wear of the motor, can be inferred.

In an alternative variant of this additional preferred embodiment, n, I, Rp, dV/dt are measured by the control unit at a set speed of rotation n (speed of rotation working point 2), and a variation is subsequently measured and analyzed by means of another maneuver at two additional speed of rotation working points to determine n, I, Rp, dV/dt at a speed rotation reduced by a speed of rotation deviation Δn (speed of rotation working point 1) and at a speed of rotation increased by the speed of rotation deviation Δn (speed of rotation working point 3). Essentially linear changes are typically obtained in relation to one another between the variables n and I when considering the three speed of rotation working points (n−Δn, n, n+Δn). The value for the pneumatic resistance Rp remains nearly constant at all three speed of rotation working points in the error-free case. The control unit carries out these maneuvers to determine n, I, Rp, dV/dt with the three speed of rotation working points in the first and/or second operating state, i.e., during the operation of the pumping device, and analyzes the results. If the pneumatic resistance Rp does not remain constant as a function of the speed of rotation n and the speed of rotation n of the pump or the pump current I do not show a linear characteristic, a defect in the pump system, for example, wear of the motor, can be inferred. Based on this analysis, the control unit determines the indicator of readiness of the pumping device to operate in this additional preferred embodiment configured in the above-described two alternatives for analyzing the characteristic. The indicator of readiness of the pumping device to operate may optionally be outputted as a message (see Table 2) in the form of a warning to replace the pump or the pumping device.

In summary, the essential advantage of the present invention is consequently that the functionality of the pumping device can be tested regularly during the operation of the pumping device as part of the gas-measuring system and readiness of the gas-measuring system as a whole to operate can be continuously monitored and ensured over a long operating time.

The present invention will be explained in more detail by means of the following figures and the corresponding descriptions of the figures without limitation of the general idea of the present invention. The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
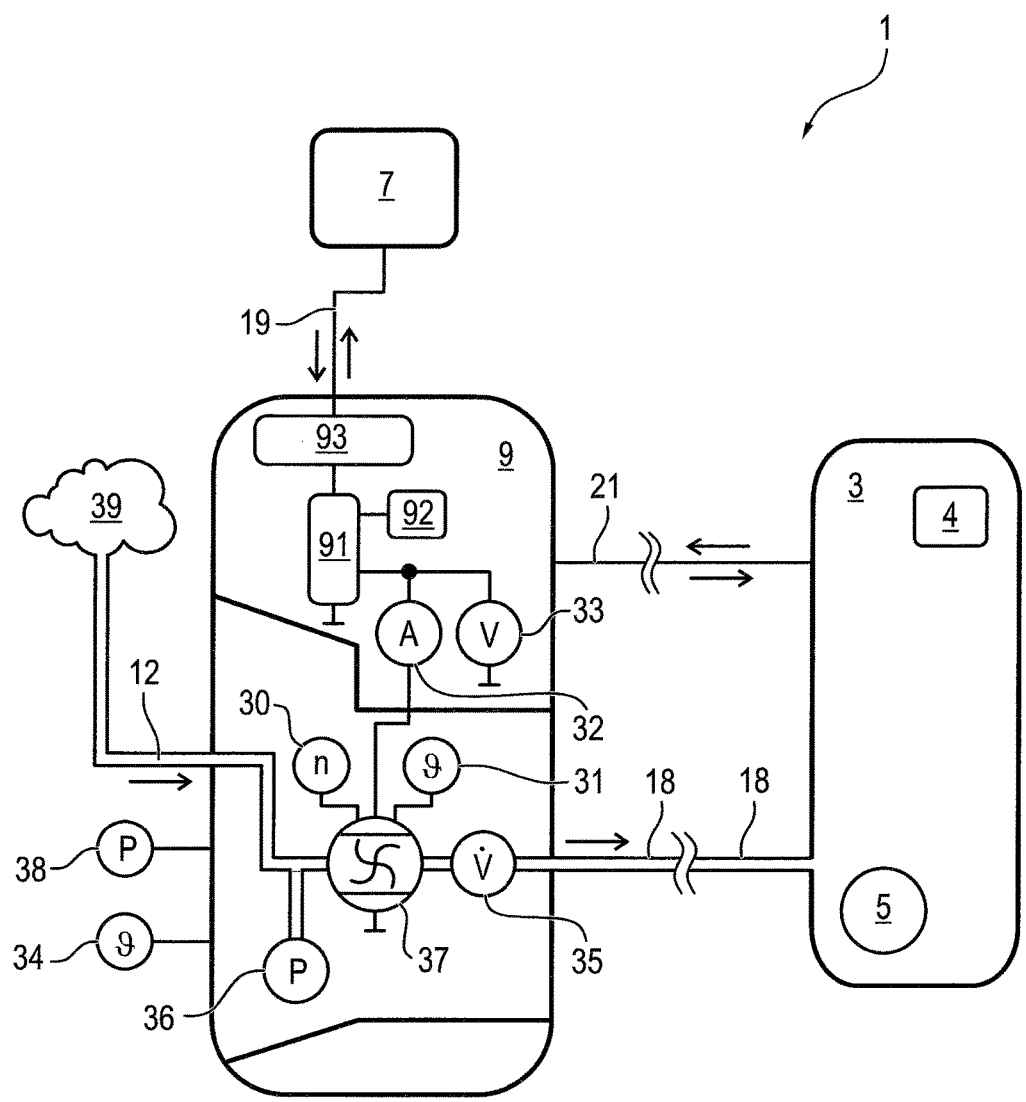
FIG. 1 is a schematic view of a pumping device according to the invention in a gas-measuring system according to the invention.

Referring to the drawings, FIG. 1 shows a gas-measuring system 1. The gas-measuring system 1 comprises a gas-measuring device 3, an analysis system 7 and a pumping device 9, wherein said pumping device 9 is connected to the analysis system 7 and to the gas-measuring device 3 by means of a data interface or data output unit 93 via data lines 19, 21. The analysis system 7 is located during use for monitoring gas concentrations or other measured ambient values in an industrial, chemical or petrochemical plant or in a mine. The gas-measuring device 3 shown in FIG. 1 is an example of a plurality of gas-measuring devices 3 at different locations, which together represent an interlinked system for monitoring ambient situations in the industrial, chemical, petrochemical or mining facility, and can together be combined, coordinated, displayed, analyzed or provided for a further processing on the analysis system 7.

The gas-measuring device 3 has a sensor 5, with which gas concentrations from the immediate vicinity of the gas-measuring device 3 can be detected. The detected gas concentrations are converted by an electronic unit 4 into data signals and are provided to the outside via data links 21.

A data output unit 93, a gas inlet 12 for test gas, resetting gas or gas to be measured, as well as a gas feed line 18 for feeding gas from the pumping device 9 to the gas-measuring device 3 are provided at the pumping device 9. In the embodiment according to FIG. 1, a quantity of gas is drawn in at the first gas inlet 12 from a measuring environment 39 by a pump 37 with a pump motor, not shown in this FIG. 1, and fed via the gas feed line 18 leading to the sensor 5 into the gas-measuring device 3. Measured data are transmitted via the data links 19, 21 from the gas-measuring device 3 to the analysis system 7. The data links 19, 21 are configured, for example, as RS232, RS485, voltage interfaces (0 . . . 10 V) or current interfaces (4 . . . 20 mA, 0 . . . 20 mA). A control unit 91, for example a programmable or memory-programmable element (µP, µC, MPC) with a corresponding memory 92 (RAM, SD card), is present in the pumping device 9, and this unit is configured to bring about the control of the pump 37 by means of control signals, for example, as a control unit or regulating unit according to a speed of rotation/pressure characteristic. A pressure sensor 36 for detecting the feed pressure generated by the pump 37, a flow sensor 35 for detecting the flow rate generated by the pump 37, a pump temperature sensor 31 for detecting the temperature of the pump 37 or of the pump motor, an ambient temperature sensor 34 for detecting an ambient temperature of the measuring environment 39, an ambient pressure sensor 38 for detecting an air pressure of the measuring environment 39, a current sensor 32 for detecting an electric operating current of the pump 37 or of the pump motor, and a voltage sensor 33 for detecting an electric operating voltage of the pump 37 or of the pump motor are provided as a sensor system in or at the pumping device 9. The sensor system is connected to control unit 91. The ambient temperature sensor 34 may also be configured in a special embodiment as a combined sensor for detecting the temperature and the humidity of the measuring environment 39. A speed of rotation n of the pump 37 or of the pump motor, which is available, for example, indirectly via the electric operating current I of the pump 37 or of the pump motor on the basis of a current or speed of rotation/pressure characteristic, or is provided by a speed of rotation sensor 30 arranged in the pumping device 9 for detecting a speed of rotation of the pump 37 or the pump motor, is available as a manipulated variable to the control unit. The sensors 30, 31, 32, 33, 34, 35, 36, 38 cooperate in conjunction with the control unit 91 in the control (control/regulation), monitoring of operating states of the pumping device 9 and the testing of the pumping device 9, especially of the pump 37 or of the pump motor, by providing measured values.

Figure 2:
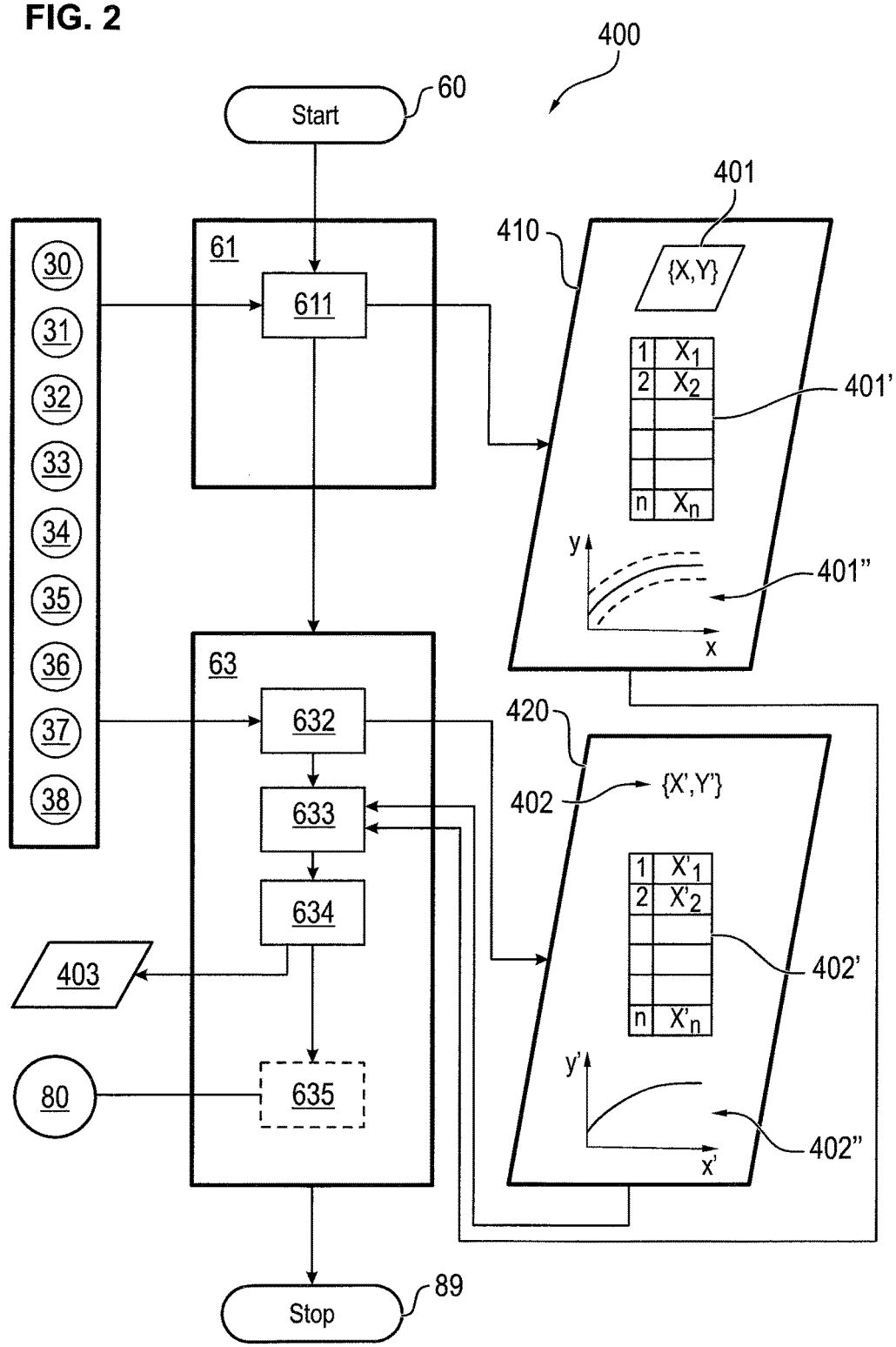
FIG. 2 is a view showing a schematic course of a method for testing a pumping device in a gas-measuring system.

FIG. 2 shows a schematic procedure 400 of the method for testing a pumping device 9 (FIG. 1) in a gas-measuring system 1 (FIG. 1) with gas-measuring device 3, analysis system 7 (FIG. 1) and control unit 91 (FIG. 1). Identical components in FIG. 1 and in FIG. 2 are designated in FIG. 2 by the same reference numbers as in FIG. 1. The control unit 91 (FIG. 1), configured, e.g., as a processor unit (µP, µC), makes possible, in conjunction with a memory 92 (FIG. 2), the implementation of the schematic procedure 400. At the start (START) 60 of the pumping device 9 (FIG. 1), the control unit 91 (FIG. 1) determines at least one first value 401, which characterizes a first operating state of the pumping device 9 (FIG. 1), in a first operating state 61 in a first step 611 from the values of the sensors 30, 31, 32, 33, 34, 35, 36, 38 shown in FIG. 1, and stores this at least one value 401 in an initialization data set 410 in the memory 92 (FIG. 1), for example, in a tabular form 401' or as a characteristic 401". In a further, second operating state 63 following the first operating state 61, the control unit 91 (FIG. 1) determines, in a second step 632, an additional value 402, 402', 402", which characterizes an additional operating state of the pumping device 9 (FIG. 1), from the values of the sensors 30, 31, 32, 33, 34, 35, 36, 38 shown in FIG. 1, and likewise stores this additional value 402, 402', 402" as an operating data set 420 in the memory 92 (FIG. 1).

In a third step 633, the control unit 91 (FIG. 1) compares the first stored value 401, 401', 401" with the additional, second stored value 402, 402', 402" from the memory 92 (FIG. 1) by means of the processor unit 91 and determines an indicator 403 of readiness of the pumping device 9 (FIG. 1) to operate in a fourth step 634 on the basis of the comparison and preferably provides this indicator 403 in an optional fifth step 635 as an error signal 80, for example, by means of a data output unit 93 (FIG. 1) as an output signal. The procedure 400 thus reaches its end (STOP) 89. Provisions are made in an optional variant for repeating the procedure 400 in an additional, second operating state 63 after the end 89 of the procedure 400 and to repeatedly determine additional operating data sets 420 in the further course and to repeatedly and regularly determine the indicator 403 of readiness of the pumping device 9 (FIG. 1) to operate.

While specific embodiments of the invention have been shown and described in detail to illustrate the application of the principles of the invention, it will be understood that the invention may be embodied otherwise without departing from such principles.

Appendix:

LIST OF REFERENCE NUMBERS

1 Gas-measuring system
3 Gas-measuring device
4 Electronic unit
5 Gas sensor
7 Analysis system
9 Pumping device
12 First gas inlet for test gas, zeroing gas or gas to be measured
17 Data input/output modules (I/O modules)
18 Gas feed line
19, 21 Data link, data signal
23 Energy supply line
30 Speed of rotation sensor
31 Pump temperature sensor
32 Current sensor
33 Voltage sensor
34 Sensor for ambient temperature sensor and/or ambient humidity
35 Flow sensor
36 Pressure sensor, feed pressure
37 Pump
38 Ambient pressure sensor
39 Environment, measuring environment (air)
60 START
61 First operating state
63 Additional/second operating state
80 Error signal, output signal
89 STOP
91 Control unit
92 Memory
93 Data interface/data output unit 400 Procedure
401, 401', 401" First value
402, 402', 402" Second value
403 Indicator of readiness to operate
410 Initialization data set
420 Operating data set
611 First step
632 Second step
633 Third step

What is claimed is:

1. A method for testing a pumping device in a gas measuring system, the method comprising the steps of:
providing the pumping device comprising a pump and a control unit arranged in the pumping device or associated with the pumping device and at least one data storage element;
determining, by the control unit, a combination of values, a pair of values or a family of values comprising at least two measured values characterizing a first operating state of the pumping device and storing the combination of values or pair of values or family of values in the at least one data storage element as an initialization data set;
determining, by the control unit, an additional combination of values, additional pair of values, or additional family of values comprising at least two additional measured values characterizing an additional operating state of the pumping device and storing the additional combination of values, additional pair of values, or additional family of values in at least one data storage element as an operating data set, wherein the additional operating state follows the first operating state in time and the at least two measured values characterizing a first operating state of the pumping device and the at least two additional measured values characterizing an additional operating state of the pumping device comprise at least two from the group of the measured values comprising: a gas feed pressure generated by the pumping device; an ambient air pressure; an ambient air humidity; an ambient air temperature; a gas flow rate or gas mass flow rate fed by the pump; a change over time in the gas flow rate or mass flow rate fed by the pump; and a velocity of gas flow generated by the pump;
comparing the initialization data set, comprised of values characterizing the first operating states of the pumping device and the operating data set comprised of values characterizing the additional operating states of the pumping device;
determining an indicator of readiness of the pumping device to operate on the basis of the comparison, wherein the indicator of readiness of the pumping device to operate is divided into categories of readiness of the pumping device to operate by means of the control unit in an additional step and the indicator with an associated category is provided as an output signal, by means of a data output unit wherein the categories comprise: a non critical change between the initialization data set and the operating data set, allowing current operation; a critical change between the initialization data set and the operating data set, in which action is required soon; and very critical change between the initialization data set and the operating data set, in which immediate action is required; and
determining an error by the control unit and generating an error signal on the basis of the categories or on the basis of the indicator of readiness to operate, wherein the error signal is provided as an output signal, by means of the data output unit, wherein the error signal represents a state concerning an error situation, a disturbance in operation of the gas measuring system or an error in signal processing, signal detection or signal output or signal supply.

2. A method in accordance with claim 1, wherein determining the combination of values characterizing a first operating state additionally includes determining, by the control unit, characterizing values for different speeds of rotation of the pump in the first operating state and storing the determined characterizing values in the initialization data set.

3. A method in accordance with claim 1, wherein the control unit is configured to perform a conversion of measured values in the first operating state based on sensed first operating state ambient conditions or in the additional operating state based on sensed additional operating state ambient conditions, or both in the first operating state and in the additional operating state based on respective sensed ambient conditions, to corresponding values based on standardized ambient conditions.

4. A method in accordance with claim 1, wherein the combination of values or family of values is further comprised of:
vacuum generated by the pump; and/or
speed of rotation of the pump; and/or
electric operating current of a pump motor arranged in the pumping device or associated with the pumping device; and/or
electric operating voltage of the pump motor.

5. A method in accordance with claim 1, wherein an initial pneumatic resistance value is determined by the control unit in the first operating state from a change over time in the gas flow rate or gas mass flow rate generated by the pump and the pressure generated by the pump, and an additional pneumatic resistance value is determined by the control unit in the additional operating state from the change over time in the gas flow rate or gas mass flow rate generated by the pump and from the pressure generated by the pump, the initial and additional pneumatic resistance values are compared with one another by the control unit, and the indicator of readiness of the pumping device to operate is determined on the basis of the comparison.

6. A method in accordance with claim 5, wherein the pneumatic resistance is determined for different speeds of rotation of the pump in the first operating state or in the additional operating state or in both in the first operating state and in the additional operating state.

7. A gas measuring system comprising:
a gas measuring device;
a gas analysis system;
an ambient condition sensor arrangement sensing at least one of ambient gas pressure, ambient gas humidity and ambient gas temperature;
data lines;
a pumping device comprising a pump, with a gas inlet and a gas outlet, and a control unit and at least one data storage element, wherein the gas inlet is configured to draw in at least ambient gas through the pump, the outlet is configured to release a pump fed quantity of a gas from the pump to the gas-measuring device, the pumping device is in data connection with the gas-measuring device and the analysis system via the data lines, and the analysis system is configured to monitor gas concentrations of amounts of gas fed to the gas measuring device by the pumping device, the control unit being configured to:

determine a combination of first values, a pair of first values or a family of first values, comprised of at least two first measured values characterizing a first operating state of the pumping device and store the at least two first measured values in the at least one data storage element as an initialization data set;

determine an additional combination of values, an additional pair of values or an additional family of values, comprised of at least two additional measured values characterizing an additional operating state and store the at least two additional values in the at least one data storage element as an operating data set, wherein the additional operating state follows the first operating state in time, wherein the values characterizing the first operating states of the pumping device of the initialization data set and the values characterizing the additional operating states of the pumping device the operating data set are two or more of: a gas feed pressure generated by the pumping device; a gas flow rate or gas mass flow rate fed by the pump; a change over time in the gas flow rate or gas mass flow rate fed by the pump; a velocity of gas flow generated by the pump; a vacuum generated by the pump; a speed of rotation of the pump; an electric operating current of a pump motor arranged in the pumping device or associated with the pumping device and an electric operating voltage of the pump motor;

receive a sensed ambient condition comprising at least one of ambient gas pressure, ambient gas humidity and ambient gas temperature during the first operating state and receive a sensed ambient condition comprising at least one of ambient gas pressure, ambient gas humidity and ambient gas temperature during the additional operating state and include the first operating state sensed ambient condition in the initialization data set and include the additional operating state sensed ambient condition in the operating data set;

compare the initialization data set and the operating data set; and determine an indicator of readiness of the pumping device to operate on the basis of the comparison including based on the first operating state sensed ambient condition and based on the additional operating state sensed ambient condition and providing the indicator as an output signal, by means of a data output unit.

8. A gas measuring system in accordance with claim 7, wherein the indicator of readiness of the pumping device to operate is divided into categories by means of the control unit in an additional step and the indicator is output with an associated category as an output signal, by means of a data output unit, wherein the categories comprise: a non critical change between the initialization data set and the operating data set, allowing current operation; a critical change between the initialization data set and the operating data set, in which action is required soon; and very critical change between the initialization data set and the operating data set, in which immediate action is required.

9. A gas measuring system in accordance with claim 8, wherein an error signal is determined by the control unit on the basis of the categories or on the basis of the indicator of readiness to operate, and the error signal is provided as an output signal by means of a data output unit, wherein the error signal represents a state concerning an error situation, a disturbance in operation of the gas measuring system or an error in signal processing, signal detection or signal output or signal supply.

10. A gas measuring system in accordance with claim 7, wherein determining the first values characterizing a first operating state includes determining, by the control unit, characterizing values for different speeds of rotation of the pump in the first operating state and storing the determined characterizing values in the initialization data set.

11. A gas measuring system in accordance with claim 7, wherein the control unit is configured to perform a conversion of measured values in the first operating state based on sensed first operating state ambient conditions or in the additional operating state based on sensed additional operating state ambient conditions, or both in the first operating state and in the additional operating state based on respective sensed ambient conditions, to corresponding values based on standardized ambient conditions.

12. A gas measuring system in accordance with claim 7, wherein an initial pneumatic resistance value is determined by the control unit in the first operating state from a change over time in the gas flow rate or gas mass flow rate generated by the pump and the pressure generated by the pump, and an additional pneumatic resistance value is determined by the control unit in the additional operating state from the change over time in the gas flow rate or gas mass flow rate generated by the pump and from the pressure generated by the pump, the initial and additional pneumatic resistance values are compared with one another by the control unit, and the indicator of readiness of the pumping device to operate is determined on the basis of the comparison.

13. A gas measuring system in accordance with claim 12, wherein the pneumatic resistance is determined for different speeds of rotation of the pump in the first operating state or in the additional operating state or in both in the first operating state and in the additional operating state.

14. A gas measuring system in accordance with claim 7, wherein:

the control unit is configured to convert the measured values in the first operating state, based on sensed first operating state ambient condition, into values based on standardized environmental conditions; or the control unit is configured to convert the measured values in the additional operating state, based on sensed additional operating state ambient condition, into values based on standardized environmental conditions; or the control unit is configured to convert the measured values in the first operating state, based on sensed first operating state ambient condition, into values based on standardized environmental conditions and the control unit is configured to convert the measured values in the additional operating state, based on sensed additional operating state ambient condition, into values based on standardized environmental conditions; and the comparison is based on at least some of the values being values based on standardized environmental conditions.

15. A method for testing a gas measuring system the method comprising the steps of:

providing a gas pumping device comprising a pump and a control unit arranged in the pumping device or associated with the pumping device and at least one data storage element;

providing the pumping device with a gas inlet and a gas outlet;

providing the pumping device as a part of the gas measuring system comprising a gas measuring device, an analysis system, an ambient condition sensor arrangement sensing at least one of ambient gas pressure, ambient gas humidity and ambient gas temperature; and data lines;

configuring the gas inlet for drawing in at least ambient gas through the pump;

configuring the gas outlet for releasing a pump fed quantity of a gas from the pump to the gas-measuring device;

providing the pumping device in data connection with the gas-measuring device and the analysis system via the data lines;

determining, by the control unit, a combination of values, a pair of values or a family of values comprising at least two measured values characterizing a first operating state of the pumping device and storing the combination of values or pair of values or family of values in the at least one data storage element as an initialization data set;

determining, by the control unit, an additional combination of values, additional pair of values, or additional family of values comprising at least two additional measured values characterizing an additional operating state of the pumping device and storing the additional combination of values, additional pair of values, or additional family of values in at least one data storage element as an operating data set, wherein the additional operating state follows the first operating state in time;

providing the values characterizing the first operating states of the pumping device of the initialization data set and providing the values characterizing the additional operating states of the pumping device the operating data set as two or more of: a gas feed pressure generated by the pumping device; a gas flow rate or gas mass flow rate fed by the pump; a change over time in the gas flow rate or gas mass flow rate fed by the pump; a velocity of gas flow generated by the pump; a vacuum generated by the pump; a speed of rotation of the pump; an electric operating current of a pump motor arranged in the pumping device or associated with the pumping device; and an electric operating voltage of the pump motor;

sensing an ambient condition comprising at least one of ambient gas pressure, ambient gas humidity and ambient gas temperature during the first operating state and including the first operating state sensed ambient condition in the initialization data set and sensing an ambient condition comprising at least one of ambient gas pressure, ambient gas humidity and ambient gas temperature during the additional operating state and including the additional operating state sensed ambient condition in the operating data set;

comparing the initialization data set, comprised of values characterizing the first operating states of the pumping device and the operating data set comprised of values characterizing the additional operating states of the pumping device; and determining an indicator of readiness of the pumping device to operate on the basis of the comparison including based of the first operating state sensed ambient condition or based on the additional operating state sensed ambient conditions or based on the first operating state sensed ambient condition and based on the additional operating state sensed ambient condition and providing the indicator as an output signal, by means of a data output unit.

16. A method for testing a gas measuring system according to claim 15, wherein:

the control unit is configured to convert the measured values in the first operating state, based on sensed first operating state ambient condition, into values based on standardized environmental conditions; or the control unit is configured to convert the measured values in the additional operating state, based on sensed additional operating state ambient condition, into values based on standardized environmental conditions; or the control unit is configured to convert the measured values in the first operating state, based on sensed first operating state ambient condition, into values based on standardized environmental conditions and the control unit is configured to convert the measured values in the additional operating state, based on sensed additional operating state ambient condition, into values based on standardized environmental conditions; and the comparison is based on at least some of the values being values based on standardized environmental conditions.

17. A method for testing a gas measuring system in accordance with claim 15, wherein the indicator of readiness of the pumping device to operate is divided into categories by means of the control unit in an additional step and the indicator is output with an associated category as an output signal, by means of a data output unit, wherein the categories comprise: a non critical change between the initialization data set and the operating data set, allowing current operation; a critical change between the initialization data set and the operating data set, in which action is required soon; and a very critical change between the initialization data set and the operating data set, in which immediate action is required.

18. A method for testing a gas measuring system in accordance with claim 17, wherein an error signal is determined by the control unit on the basis of the categories or on the basis of the indicator of readiness to operate, and the error signal is provided as an output signal by means of a data output unit, wherein the error signal represents a state concerning an error situation, a disturbance in operation of the gas measuring system or an error in signal processing, signal detection or signal output or signal supply.

* * * * *